United States Patent [19]
Chapelon

[11] Patent Number: 5,743,863
[45] Date of Patent: *Apr. 28, 1998

[54] HIGH-INTENSITY ULTRASOUND THERAPY METHOD AND APPARATUS WITH CONTROLLED CAVITATION EFFECT AND REDUCED SIDE LOBES

[75] Inventor: Jean-Yves Chapelon, Villeurbanne, France

[73] Assignee: Technomed Medical Systems and Institut National, Vaux en Velin

[*] Notice: The term of this patent shall not extend beyond the expiration date of Pat. No. 5,573,497.

[21] Appl. No.: 720,555

[22] Filed: Oct. 2, 1996

Related U.S. Application Data

[63] Continuation of Ser. No. 396,160, Feb. 28, 1995, Pat. No. 5,573,497, which is a continuation-in-part of Ser. No. 307,719, Nov. 30, 1994, abandoned.

[30] Foreign Application Priority Data

| Jan. 22, 1993 | [FR] | France | 9300662 |
| Jan. 3, 1994 | [FR] | France | 9402322 |
| Jan. 21, 1994 | [WO] | WIPO | PCT/FR94/00070 |

[51] Int. Cl.⁶ ........................... A61B 17/00
[52] U.S. Cl. ............................ 601/2; 601/3
[58] Field of Search ............ 128/660.03; 601/2, 601/3; 607/97

[56] References Cited

U.S. PATENT DOCUMENTS

| 3,866,068 | 2/1975 | Krenicki et al. | |
| 5,501,655 | 3/1996 | Rolt et al. | 601/2 X |
| 5,573,497 | 11/1996 | Chapelon | 601/2 |

FOREIGN PATENT DOCUMENTS

| 0274136 | 12/1987 | European Pat. Off. |
| 2685211 | 12/1991 | France |
| 2524555 | 5/1975 | Germany |

OTHER PUBLICATIONS

"Effects of cavitation in the high intensity therapeutic ultrasound", *Proceedings of 1991 Ultrasonics Symposium*, vol. 1, Dec. 1991, pp. 1357–1360.

"Cavitation threshold measurements for microsecond long pulses of ultrasound", *Journal of the Acoustical Society of America*, vol. 83, No. 6, Jun. 1988, pp. 2190–2201 Copy of international search report.

*Primary Examiner*—Francis Jaworski
*Attorney, Agent, or Firm*—Welsh & Katz, Ltd.

[57] ABSTRACT

In a high-energy ultrasound therapy method and apparatus, said apparatus comprises a therapy device with at least one ultrasound therapy transducer element and a signal generator supplying an electronic signal to said ultrasound transducer element, the signal generator supplying the transducer(s) with a wideband electronic signal of the random or pseudo-random type.

22 Claims, 5 Drawing Sheets

HIGH-INTENSITY ULTRASOUND THERAPY METHOD AND APPARATUS WITH CONTROLLED CAVITATION EFFECT AND REDUCED SIDE LOBES

This patent application is a continuation of U.S. Ser. No. 08/396,160, entitled High Intensity Ultrasound Method and Apparatus with Controlled Cavitation Effect and Reduced Side Lobes, filed on Feb. 28, 1995 and issued as U.S. Pat. No. 5,573,497. U.S. Ser. No. 08/396,160 claims priority based on French Patent Application No. 94/02322 dated Mar. 1, 1994 and is a continuation-in-part of U.S. Ser. No. 08/307,719 and filed on Nov. 30, 1994 and now abandoned, which is based on PCT/FR94/00070 dated Jan. 21, 1994 which claims priority based on French Patent Application No. 93/00662 dated Jan. 22, 1993. The subject application claims priority based on all of the above United States and foreign applications.

BACKGROUND OF THE INVENTION

The present invention relates to a therapy method and apparatus for generating high-intensity ultrasound with control of cavitation effect, and to the use of this method and apparatus for reducing secondary lobes set up by a periodic-type structure.

It is known that ultrasound therapy, using a piezoelectric transducer driven by sinewave-type electronic signals makes it possible to create tissue lesions through tissue heating due to ultrasound absorption. Furthermore, such tissue lesions can be limited to a specific volume by carrying out therapy using focused ultrasound, which is particularly valuable for achieving effective treatment in cancer therapy such as, for example, cancer of the prostate, breast, brain, etc.

Existing hyperthermia apparatus using ultrasound heats tumors to a moderate temperature of the order of 42.5° C. for a time of the order of one hour.

Since hyperthermia treatment may be insufficient, it can be advantageous to attempt to obtain much higher temperatures, for example of around 80° C., with a view to sensitizing cells or completely destroying them. To achieve this, it is necessary to supply acoustic energy to the tissue over a brief period, generally of the order of a few seconds, in order, notably, to avoid heat loss by natural transfer, notably due to blood circulation, throughout the tissue. Sufficient energy needs to be used and this implies using high ultrasound intensity.

This however brings one up against the technical problems resulting from cavitation phenomena which become even more accentuated as acoustic intensity increases, as has been described in detail by K. Hynynen in "The threshold for thermally significant cavitation in dog's thigh muscle in vivo" published in Ultrasound In Medicine and Biology, vol. 17, No.2, pages 157–171, (1991).

Acoustic cavitation covers any physical phenomena involving the activity of bubbles or micro-bubbles of gas undergoing movement as a result of an acoustic field.

Two types of cavitation can generally be distinguished:

stable cavitation where the walls of the bubbles are oscillating at the frequency of the ultrasound field without too great a consequence for the surrounding cells, but which considerably disturbs ultrasound transmission by reflecting or scattering incident waves. This phenomenon can appear at very low pressure levels as soon as bubbles are present in the medium;

transitory cavitation where bubbles expand up to their resonant size, and than implode violently. In this case, the energy accumulated by the bubbles is simultaneously released in the form of a shock wave, with intense heat (generally from 1000° to 20000° K) and microjets that can reach speeds of 100 m/s. All this leads to the creation of free radicals and mechanical destruction of surrounding tissue. Generally, this phenomenon appears starting from high incident pressures which thus defines the cavitation threshold.

Every living medium contains a certain amount of dissolved gas present in the form of bubble micronuclei Under the effect of an ultrasound field, the nuclei expand through a physical phenomenon known as rectified diffusion to reach a critical size known as the Blake threshold.

The inventor showed a while ago in an article entitled "Effects of cavitation in high intensity therapeutic ultrasound" published on pages 1357 to 1360 of volume 2 (1991) of "Ultrasonics Symposium Proceedings" (published by B. R. McAvoy) that the use of intensities that were too high, generally above 3000 W/cm$^2$ reduced the therapeutic effects of thermal treatment involving tissue destruction. This phenomenon can be explained by supposing that at these intensities, cavitation bubbles which may appear ahead of the focal spot act as a screen for incident ultrasound waves. Moreover, with the specific aim of reducing cavitation effects, F. J. Fry stated in International Patent application WO-A-89/07909 that it is necessary to inhibit production of micro-bubbles in the primary focal site to avoid lesions appearing outside said site (see page 15 of said Patent application). Under these conditions, it is stated that the intensity should not exceed 300 W/cm$^2$ at a 1 MHz frequency, or 2,100 W/cm$^2$ at 4 MHz.

K. Hynynen also showed in the above-cited article that an intensity of 700 W/cm$^2$/MHz should be considered as a maximum value to be used in hyperthermia treatment as, at higher levels, cavitation leads to unpredictable energy absorption.

To sum up the state of the art, cavitation hinders penetration of acoustic waves into tissue thus preventing treatment from following predictable lines. Moreover, cavitation can lead to uncontrolled tissue destruction, outside the target volume. It is thus appropriate, regardless of the application envisaged (in other words thermal treatment at high temperature for tissue destruction, or at moderate temperature or hyperthermia), to increase cavitation onset thresholds.

To avoid cavitation, the only recommendations that can be found in the prior art consist either in reducing acoustic intensity, or emitting in a discontinuous manner, using wave trains of determined duration, and respecting a waiting time between the trains, or, yet again, increasing emission frequency.

However, reducing acoustic intensity or using discontinuous emission leads to a loss of acoustic energy transmitted to the medium, which limits temperature rise or increases treatment duration. Furthermore, increasing emission frequency limits the depth of treatment, absorption by tissue being directly proportional to frequency, as described by Daniels et al., in the journal "Ultrasound in Medicine and Biology" vol. 13, No.9, (1987) in the article entitled "Ultrasonically induced gas bubble production in agar based gels".

It should also be noted that, in the prior art, continuous sinewaves are employed for tissue heating, and thus emission duration is far higher than signal period. Usually, insonification of tissue for several seconds at a frequency comprised between 1 and 5 MHz is envisaged.

Certain authors have, on the other hand, considered using acoustic waves of a pulsed type, with a duration of the order of several periods, in other words several microseconds, but

3 for a completely different purpose, specifically either the destruction of concretions (lithotritation), or for diagnosis (Doppler ultrasound scanning).

The cavitation phenomena produced by such pulses have been studied. For example, Fowlkes and Crum in an article entitled "Cavitation threshold measurements for microsecond length pulses of ultrasound" published in J. Acoustic Soc. Am. 83 (6), June 1988, investigates the evolution of cavitation threshold as a function of pulse width and pulse frequency. Similarly, Delius, while studying cavitation produced by lithotripters recommended reducing acoustic wave repetition rates (see "Effects of lithotripter shock waves on tissue and materials", Frontiers on non-linear acoustics, edited by M. F. Hamilton and D. T. Blackstock, Elsevier Science Publishers, London 1990).

However, pulse methods do not make it possible to produce a temperature rise in tissue since each pulse only transports small amount of energy, and the pulses need to be spaced. It is thus not possible to assimilate work done with these waves with the work at the basis of this present invention.

SUMMARY OF THE INVENTION

Thus, the principle aim of the present invention is to resolve the new technical problem of providing a solution enabling maximum energy to be supplied to the medium, preferably the tissue of a living being, in particular an animal or human being, in the shortest possible time and preferably reducing or preventing the occurrence of cavitation phenomena.

A further aim or the invention is to resolve the new technical problem of providing a solution enabling maximum energy to be supplied to the medium, preferably the tissue of a living being, in particular an animal or human being, in the shortest possible time, while simultaneously ensuring safe and effective control of heat deposit, thus making it possible either to provide moderate thermal treatment in the framework of hyperthermia, or to carry out thermal treatment at high temperatures to achieve tissue destruction, preferably reducing or limiting cavitation phenomena.

Moreover, the invention resolves the new problem of secondary focusing which can occur when periodic or quasi-periodic structures are present on the path between the emission device and the region to be treated.

The present invention has the further aim of resolving the above technical problems in a simple, reliable, inexpensive manner making widespread industrial and medical use possible.

The present invention provides a satisfactory solution for the first time to the technical problems defined above, and has further technical advantages which will become more clear from the detailed description which follows, including the attached drawings which constitute an integral part thereof.

Thus, according to a first aspect, there is provided a method for generating ultrasound waves in a propagation medium comprising activating at least one ultrasound transducer element by an electronic signal supplied by a signal generator and reducing or preventing cavitation phenomena resulting from the propagation of ultrasound waves emitted by the ultrasound transducer element within the propagation medium by the use of a signal generator supplying a wideband electronic signal.

In this invention, in other words in the description and claims, the expression "wideband" for the spectrum of an electronic signal means that signal spectrum bandwidth is about 50% of the central frequency. For example, for a signal of central frequency 2 MHz, the bandwidth will be around 1 MHz and will thus cover frequencies varying from about 1.5 MHz to about 2.5 MHz.

In a preferred embodiment, a signal generator supplying a continuous random or pseudo-random electronic signal is employed.

Throughout this specification, the term "continuous" should be taken to mean that the duration of emission of the signal is very much longer than the period of the signal, as has already been said in the introduction above.

According to one preferred feature, the abovesaid signal generator supplies a pseudo-random electronic signal of the Gaussian or Poissonian distribution type. Such signal can typically be obtained from a source of thermal noise amplified by electronic amplification.

According to a further advantageous feature, the signal generator supplies a pseudo-random electronic signal using Golay coding.

According to a further advantageous feature, the signal generator supplies a pseudo-random electronic signal using Barker coding.

According to still a further advantageous feature of the invention, the signal generator supplies a coded electronic signal of M-sequence pseudo-random type.

M-sequence signals also referred to as maximum length binary sequences are of the type described by Jean-Yves Chapelon in Chapter 6, on pages 225 to 236, particularly page 230 onwards of the book "Progress in medical imaging" edited by Professor Newhouse and published by Springer Verlag, New York, 1988 which is incorporated herein by reference.

Such M-sequence or Golay or Barker pseudo-random coded signals can be employed directly or can phase- or frequency-modulate an electronic signal the carrier frequency of which corresponds to the transducer's nominal operating frequency.

Coded signals of the M-sequence pseudo-random type are particularly preferred. Such signals are precisely described in "Progress in medical imaging". Briefly, they consist of binary signals built up by pseudo-random repetition of pulses of elementary duration. Each of said sequences is repeated with a repetition period T that is characteristic of the M sequence.

Figure 4:
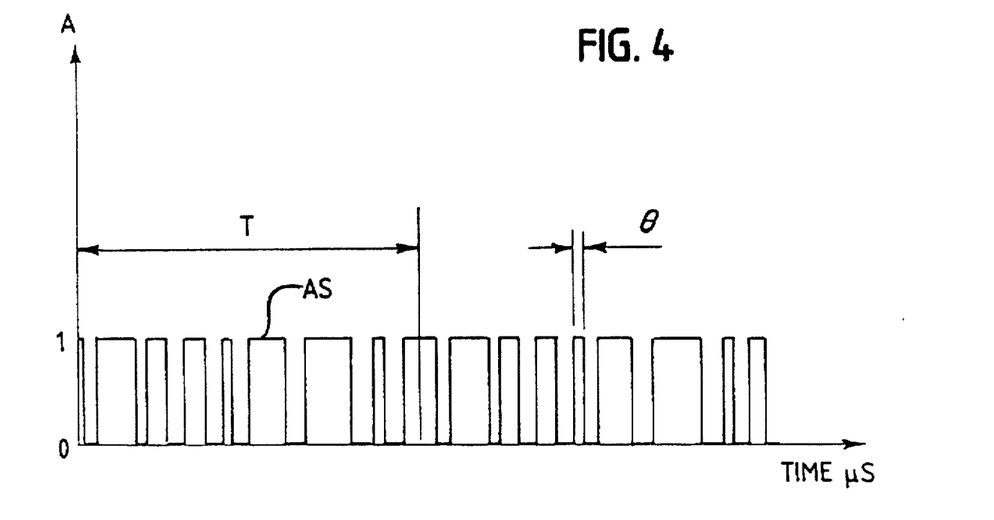

A more precise description of an M sequence signal can be provided with reference to FIG. 4 attached:

elementary pulse duration "θ" $0.1 \, \mu s < \theta < 100 \, \mu s$, ideally about 1 μs, repetition period T: $1 \, \mu s < T < 10 \, s$, ideally comprised between 0.5 and 5 s.

The pseudo-random type coded signals, particularly the currently preferred M sequence pseudo-random type signals can readily be obtained using electronic circuits well known to those skilled in the art.

The use of such wideband electronic signals, preferably random or pseudo-random, makes it possible to achieve better control of heat deposition and to avoid temperature increase disturbance by secondary effects such as cavitation, thus enabling spontaneous tissue destruction to be avoided particularly in the case of moderate heating used in hyperthermia.

Secondly, considering high-intensity use, the invention makes it possible to employ higher intensities and to reduce, for a given ultrasound dose, firing duration and, consequently, the duration of treatment, while avoiding cavitation phenomena thus making it possible to carry out treatment of tumors in living beings, in particular animals or human beings, with higher level of safety while reducing the risk of damage at various interfaces.

From a second aspect, the present invention also provides a therapy apparatus comprising an actual therapy device including at least one ultrasound therapy transducer element and a signal generator supplying an electronic signal to said ultrasound transducer element, in which the signal generator supplies a wideband electronic signal of the random or pseudo-random type.

In one preferred embodiment, the signal generator supplies a Gaussian or Poissonian distribution type random signal.

In another preferred embodiment, the signal generator supplies a Golay coded or a Barker coded pseudo-random signal.

In another preferred embodiment, the signal generator supplies an M-sequence pseudo-random type coded electronic signal.

This M-sequence pseudo-random type coded electronic signal preferably has an elementary pulse duration (θ) theta comprised between 0.1 µs and 100 µs and is ideally of about 1 µs, and a period of repetition T about between 1 µs and 10 s and ideally about between 0.5 s and 5 s.

In either aspect of the invention, to increase the effectiveness of cavity effect reduction or prevention, an ultrasound transducer which preferably is itself wideband, is used, in other words the ultrasound transducer generates ultrasound waves when excited by a signal the frequency of which is substantially different from its nominal frequency.

Usually, two types of transducer can be used for generating continuous ultrasound waves for therapeutic purposes. These comprise, firstly, conventional ultrasound transducers essentially consisting of piezoelectric ceramic. Such ceramics have an acoustic impedance which is very different from that of the propagation medium and, as a result of this, their coupling with said medium is poor. This results in strong vibrations of the ceramic when it is excited by an electric signal, the resulting ultrasound transducer having a narrow frequency bandwidth.

For therapy carried out to date using ultrasound waves, such transducers are suitable as the control signals are themselves of the narrow band type.

In the framework of this invention, the frequency band of the ultrasound transducers is widened by the application of different types of treatment to the ceramic surface, these modifying ultrasound coupling with the propagation medium. Particularly, a layer of materials having an acoustic impedance intermediate between that of ceramic and the propagation medium of appropriate thickness is deposited in this case on the ceramic, such a layer being referred to as a quarter-wave layer. A so-called backing layer could also be deposited on the back of the ceramic between the latter and the air. These two types of treatment of the ceramic enable a wideband ultrasound transducer to be obtained.

Another type of wideband transducer can be obtained using composite type materials, this being particularly suitable for implementation in the present invention for reducing or preventing cavitation effects.

This makes it possible to obtain the determining technical advantages stated above.

According to a further aspect, the invention discloses the use, in a therapy apparatus including at least one ultrasound transducer and a signal generator supplying an electronic signal to said transducer, of a wideband electronic signal for reducing or preventing secondary focusing phenomena behind a periodic or quasi-periodic structure.

This for example makes it possible to treat the liver behind the rib cage by reducing or preventing lesions due to secondary focusing or side lobe phenomena.

In one embodiment of this third aspect of the invention, the wideband electronic signal is of the random or pseudo-random type.

The wideband electronic signal can be a Gaussian or Poissonian distribution type random signal.

The wideband electronic signal can also be a Barker coded or Golay coded pseudo-random signal.

For the wideband electronic signal, one can use a M-sequence pseudo-random type coded electronic signal of a frequency having an elementary pulse duration of about between 0.1 µs and 100 µs and ideally of about 1 µs, and a period of repetition T of about between 1 µs and 10 s and ideally of about between 0.5 s and 5 s.

The electronic wideband signal may also have an autocorrelation function approaching a Dirac function.

Further characteristics of the invention will become clear from the detailed description that follows, including the drawings which constitute an integral part thereof and the claims accompanying this description.

BRIEF DESCRIPTION OF THE DRAWINGS

The invention will now be described on the basis of a currently preferred embodiment thereof simply by way of illustration which in no manner should be considered as limiting the scope on the invention, with reference to the attached drawings.

DETAILED DESCRIPTION OF PREFERRED EMBODIMENT

Figure 1:
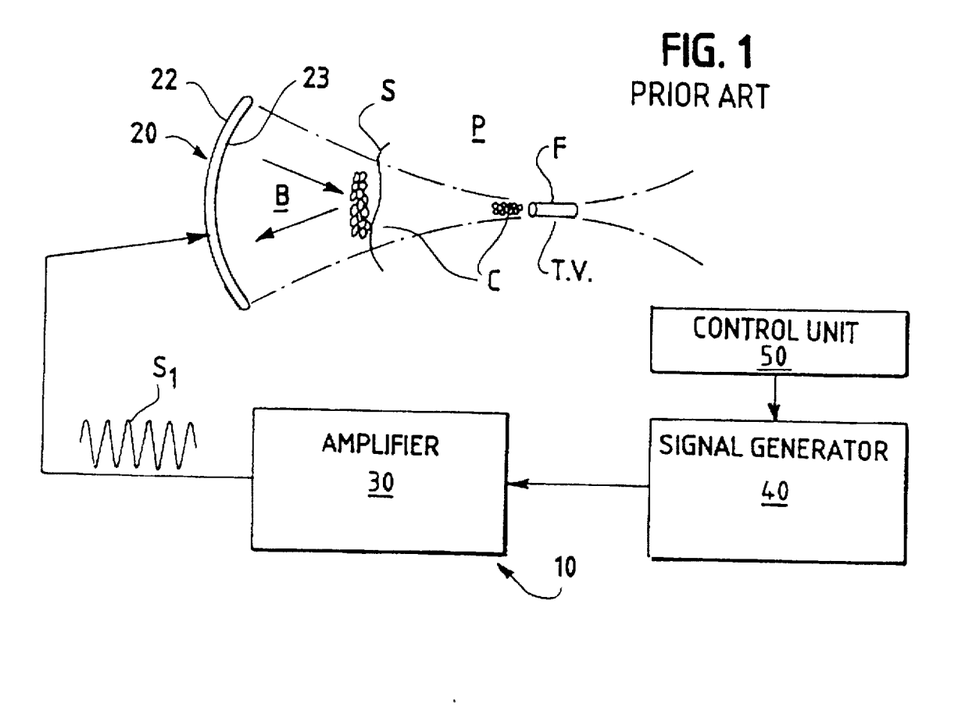
FIG. 1 is a highly schematic representation of a known therapy device for performing therapy of the tissue of a living being, including a single- or multi-transducer device having one or several piezoelectric transducers, in the form of a semi-spherical cup allowing geometrical focusing on the propagation axis visible in FIG. 2.

With reference to FIG. 1, there is shown diagrammatically a known therapy device generally identified by reference numeral 10, for carrying out therapy of the tissue of a living being.

This therapy apparatus 10 includes an actual therapy device which here takes the form of a semispherical cup 22 using natural focusing including one or several piezoelectric transducer elements, in particular a single-element piezoelectric transducer identified by reference 23 having substantially the same dimensions as the semi-spherical cup 22 as is well known to those skilled in the art, no supplementary description thereof appearing necessary. One example of an embodiment of such a therapy device is, for example, one in the form of a semi-spherical cup 22 of 100 mm diameter, using natural focusing at a focal length of 100 mm, with an operating frequency of about 1 MHz, using one single piezoelectric transducer element 23.

Transducer element 23 is linked, via an amplifier device 30, to a signal generator 40 which can itself be controlled by a control unit 50.

It should be noted that, in accordance with another possible embodiment, semi-spherical cup 22 using natural focusing can be subdivided into an annular array, well known to those skilled in the art, or into a mosaic also known to those skilled in the art, and no supplementary description thereof appears necessary. In this case, each individual annular or mosaic-like transducer element is linked via an amplifier device including individual amplifiers and a delay line device including individual delay lines, to a common signal generator such as signal generator 40 controlled in its turn by control unit such as control unit 50. The control unit then controls the delay lines by supplying the delay value needed by each line for obtaining focusing at the desired focal length.

Due to this design of the apparatus, dynamic electronic focusing with focal length being varied at will can be achieved.

Figure 2:
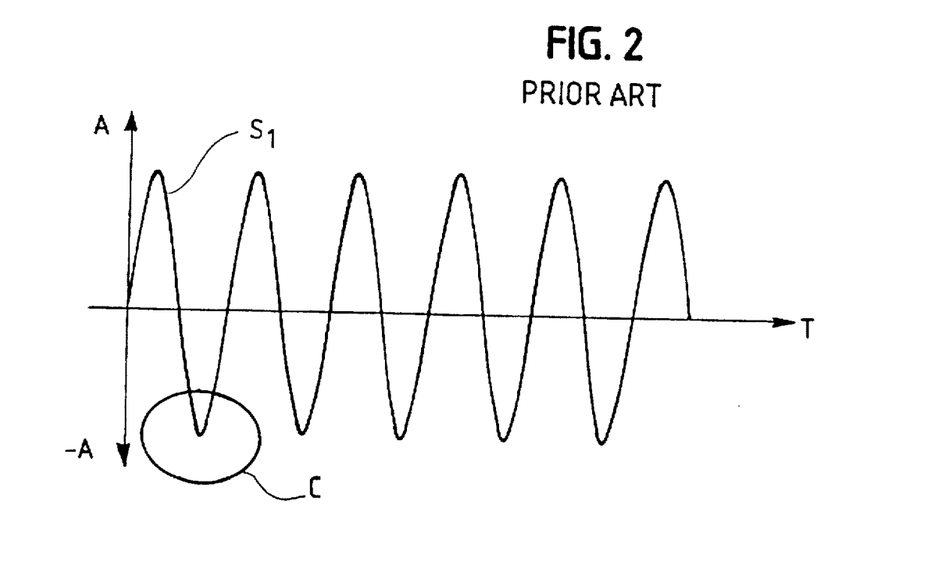
FIG. 2 shows a curve in the form of a sinewave as a function of time t on the x-axis and amplitude A on the y-axis, according to the prior art as employed in an ultrasound wave generating device of FIG. 1.

Considering the prior art apparatus of FIG. 1, when a conventional electronic signal is generated by generator 40 of the sinewave type as shown schematically at the output from amplifier 30 and, in more detail, in FIG. 2, for example at a frequency of around 1 MHz, natural focusing is obtained in the focal region F defining the treatment volume T.V.

With such a continuous sinewave signal, in other words one having a duration distinctly higher than the frequency value per period, which in general is several seconds compared to a 1 MHz frequency, bubbles of gas present in tissue or which are spontaneously generated by ultrasound waves, identified by reference B, which are present ahead of the various interfaces, for example of focal region F or the interface with the skin S of the patient P, will start oscillating after several pulses at frequency $f_p$, called the pumping frequency. The diameter of the gas bubbles B will increase at each pulse due to the so-called rectified diffusion phenomenon, to reach a maximum value that is characteristic of the frequency $f_p$, or Blake threshold. When the acoustic field intensity exceeds the cavitation threshold, which practically always is the case in therapeutic treatment, the bubbles will implode releasing energy. This cavitation threshold is identified by the general reference character C on FIG. 2 for sinewave signal intensities of relatively high amplitude.

This constitutes a major disadvantage in the state of the art.

Figure 3:
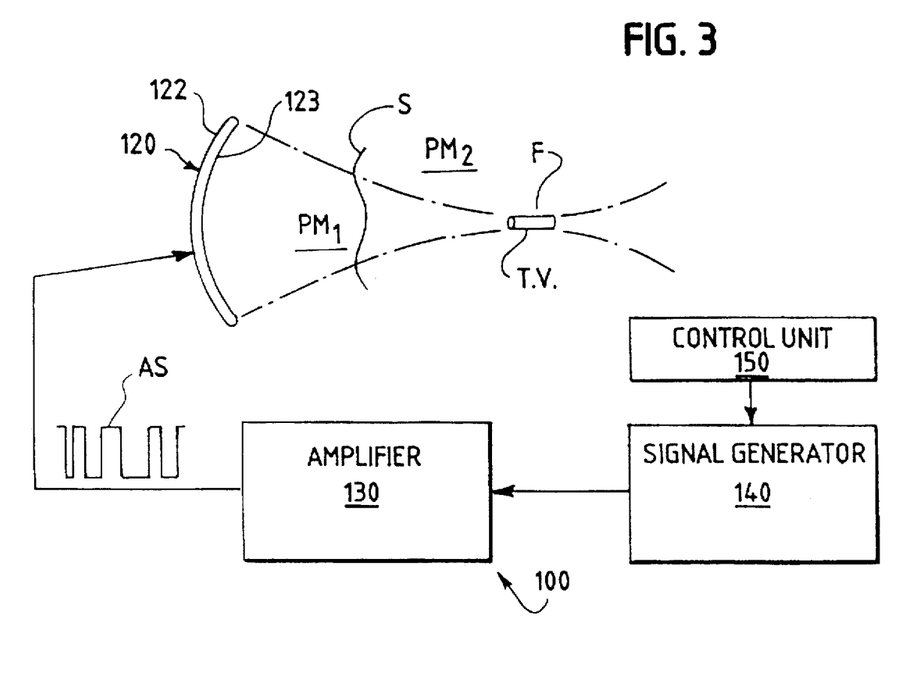
FIG. 3 is a highly schematic view of a therapy device according to the present invention for carrying out therapy of living being tissue, including a wideband electronic signal generating device, said signal being preferably random or pseudo-random, delivered to the piezoelectric transducer device for generating an ultrasound wave, the random or pseudo-random signal being shown diagrammatically in FIG. 3, and in detail in FIG. 4 as a function of time expressed in microseconds on the x-axis, with amplitude on the y-axis.

Under these conditions, and with reference to FIG. 3, an apparatus according to the present invention is shown generally identified by reference numeral 100. The same reference numerals increased by 100 have been used to identify those parts that are identical, or operate identically, to those in the prior art apparatus. Thus, the actual therapy device is here identified by the reference 120, the semi-spherical cup by 122 and the piezoelectric transducer element by 123, the amplifier device by 130 and the electronic signal generator device and control unit by 140 and 150 respectively.

In the framework of the apparatus according to the invention, the signal generator device 140 supplies a wideband electronic signal, identified by the reference A.S. shown on FIG. 3, at the output from amplifier device 130, this being shown in more detail on FIG. 4.

For this invention, the ultrasound transducer can itself be a wideband device, implemented as described previously.

In the invention and for providing an endorectal probe for prostate treatment, it is preferred to use a transducer in the form of a semi-spherical cup of about 35 mm diameter using natural focusing at the focal length of 35 mm, while, preferably, a signal having a central frequency of about 2.25 MHz is employed.

As has been said above, the term wideband spectrum in this present description and claims should be taken to mean that the bandwidth of the signal spectrum is about 50% of the central frequency. For example, for a signal having a central frequency of 2 MHz, bandwidth will be about 1 MHz and will thus comprise frequencies from about 1.5 MHz to about 2.5 MHz.

In the invention, more particularly for the purpose of reducing or preventing cavitation phenomena resulting from the propagation of ultrasound waves emitted by the ultrasound transducer element 123 in the propagation medium PM1, PM2, signal generator 140 supplies a random or pseudo-random wideband electronic signal, identified by reference A.S. in FIGS. 3 and 4. The central frequency is generally comprised between 20 MHz and 0.5 MHz.

It will be noted that, in the framework of the invention, the use of random or pseudo-random signals provides an excitation ultrasound field spectrum consisting of a multiple-frequency spectrum, the random appearance characteristic of which limits bubble growth, so that the latter rarely attain the critical diameter above which cavitation effects occur.

Thus, the invention makes it possible to limit or prevent cavitation phenomena.

The random or pseudo-random signal supplied by signal generator 140 is of the type described above and can, for example, be a Golay or Barker coded pseudo-random electronic signal, these being well known to those skilled in the art, particularly from the preceding description.

An M-sequence pseudo-random coded electronic signal can also be employed, this preferably having an elementary pulse duration (θ) theta, about between 0.1 μs and 100 μs, and a repetition period T about between 1 μs and 10 s.

A random signal of a Gaussian or Poissonian distribution type can also be employed.

It should be noted that the electronic signal shown in FIG. 3 and in detail in FIG. 4 is an M-sequence pseudo-random electronic signal the period of which T is comprised between 1 μs and 10 s the elementary pulse duration theta (θ) being about between 0.1 μs and 100 μs.

Figure 5:
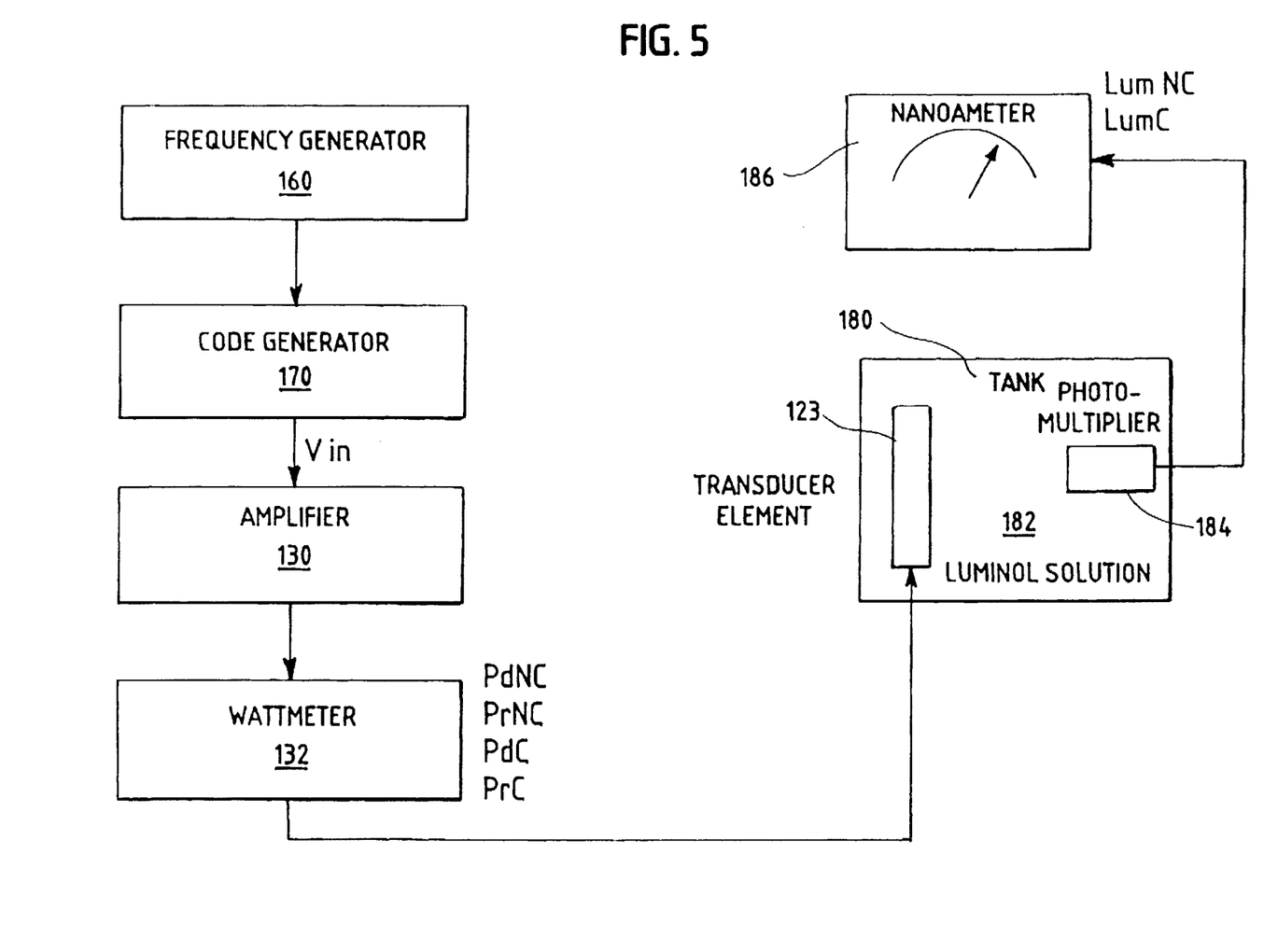
FIG. 5 is a block diagram of a setup making it possible to clearly bring to light reduction in cavitation by using a random or pseudo-random type electronic signal for exciting the ultrasound transducer.

With reference to FIG. 5, there is here shown an apparatus making it possible to demonstrate reduction in cavitation when electronic signals, or pseudo-random codes according to the present invention are employed, is thanks to the use of a luminol. This chemical compound is known to emit photons (fluorescence) when in the presence of cavitation, as described in the article by Fowlkes et al. in J. Acoust Soc. Am. vol. 83 of June 88 page 2190–2200 entitled "Cavitation threshold measurements for microsecond length pulses of ultrasound".

This apparatus includes, in the schematic form of FIG. 5, a frequency generator 160 associated with a code generator 170, the combination of the two generators 160 and 170 corresponding to the electronic signal generator 140 of FIG. 3, coupled to an amplifier device 130 for supplying a pseudo-random or random type electronic signal according to the present invention, for example an M-sequence signal, to transducer element 123 placed in a tank 180 containing a solution of luminol 182. In the luminol solution 182, not only is transducer 123 immersed, but a photomultiplier 184 device is also present, connected to a moving-needle nanoammeter 186 providing a measurement in nanoamperes proportional to the photoluminescence obtained using the luminol.

The luminol solution 182 is obtained from a solution of demineralized distilled water, saturated with air at atmospheric pressure, and of luminol (aminophtalhydrazide, 1.4 mmol previously dissolved in hplc-grade dimethylsulfoxide (DMSO)). The solution was buffered with CAPS (3-cyclohexylamino 1-propane sulfonic acid), 25 mmol and balanced to a pH of 10 with 0.1M soda.

For this experiment, the ultrasound transducer element 123 employed had a diameter of 5 cm, and focused to 97 mm. The tank was a cylindrical 40 ml container arranged horizontally, with a length of 5 cm in which focusing effects did not participate, the energy being distributed throughout the tank. Transducer resonant frequency was 1.11 MHz, said value being obtained at the sonoluminescence maximum of the water.

The photomultiplier is for example Hamamatsu type R374 comprising a lens optical system for receiving the fluorescence emitted by the luminol. Tank 180 was optically isolated to avoid any light interference. Photomultiplier 184 was powered by a small generator not shown here and the light signal was read on the ammeter 186 that integrated the total amount of light emitted by the luminol.

Transducer 123 was connected to power amplifier 130, which, for example, is of the Ampar 801, Prana, having a passband ranging from 0.1 to 1.8 MHz. The electronic signal or M-sequence pseudo-random code generator was manufactured by the INSERM having a period T of about 60 ms, and an individual pulse duration (θ) of 1.8 μs, and was synchronized by a HP 8116 A type function generator. Wattmeter 132 was a Rhode & Schwarz digital wattmeter reference NAP which allowed incident and reflected power to be measured.

Regarding wattmeter 132 readings, the references indicated on FIG. 5 have the following meanings:

"PdNC"=direct power from an uncoded signal, in other words a sinewave signal of the prior art;

"PrNS"=reflected power from an uncoded signal, in other words a sinewave signal of the prior art;

"PdC"=direct power from a coded signal, in other words a random or pseudo-random type signal of the invention;

"PrC"=power reflected with a coded signal, in other words a random or pseudo-random type signal of the invention.

Figure 6:
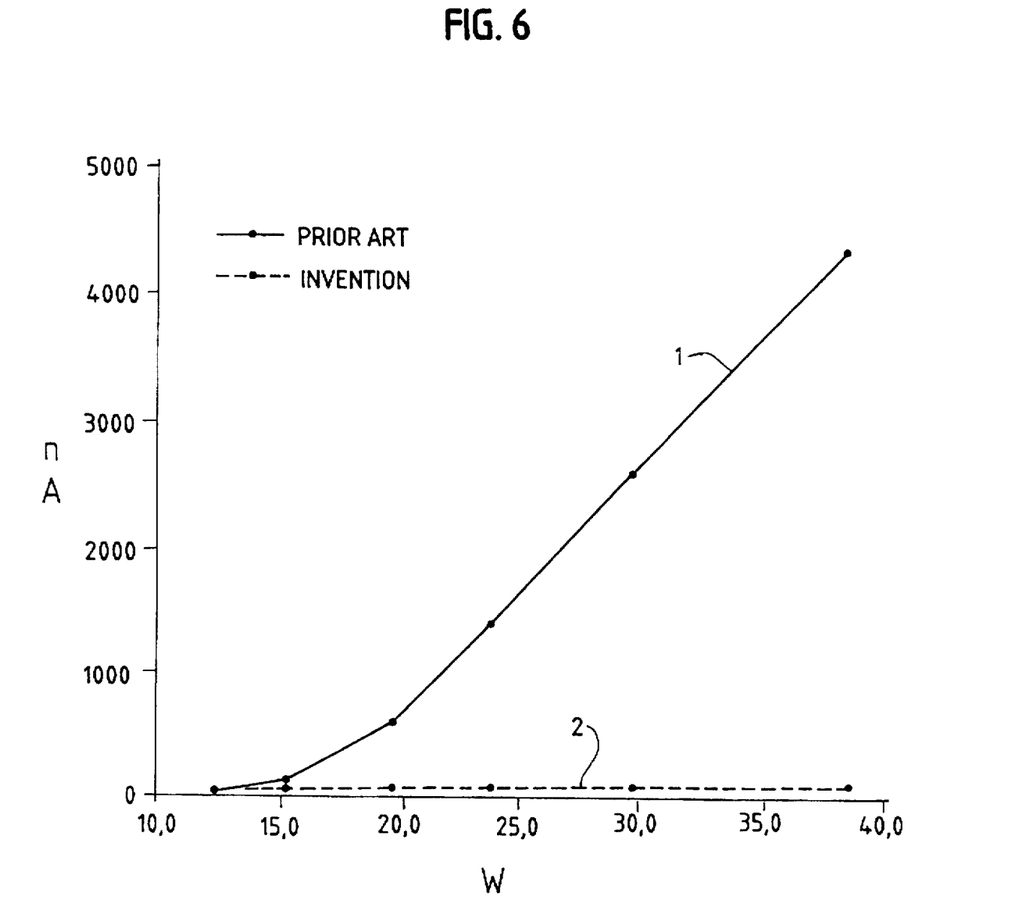
FIG. 6 shows results obtained with the apparatus in FIG. 5 in the form of a graph in which the line identified by the reference 2 corresponds to the random or pseudo-random signal according to the invention of FIGS. 3 and 4 joining the points shown by the -♦- signs, and the line bearing the reference 1 results from the use of a sinewave signal according to the prior art employed in FIGS. 1 and 2, and joining the points -•-, as a function of power transmitted by the transducer expressed in Watts on the x-axis, the value in nanoamperes provided by an ammeter integrating the total amount of light emitted by the luminol employed being indicated on the y-axis.

Measurement were made at different powers, firstly with an uncoded signal (NC) (monochromatic signal at 1.11 MHz) or continuous sinewave of the prior art, such as signal $S_1$ of FIGS. 1 and 2, which enabled line 1 to be obtained shown by the circles or dots in FIG. 6 for comparative purposes. Secondly, this same signal modulated with a pseudo-random code made it possible to obtain an M-sequence pseudo-random electronic signal according to the invention, as shown in FIGS. 3 and 4 bearing the reference AS, which provided the line 2 identified by the diamond-shaped points on FIG. 6.

In both cases, the signal generated was maintained until a luminescence plateau was achieved. The solution was injected into the tank manually with a 50 ml syringe, this always being done in the same way.

For each power tested, measurement was repeated 4 times with the same solution. Between these four measurements, the solution was drawn off from the tank and reinjected in order to maintain a constant degree of saturation. On the other hand however, when there was a change from one power to the other, the solution was thrown away and renewed.

Temperature was relatively stable (23°–28° C.), radiation time being short and the transducer being only cooled from the back with a cold water circuit (not shown) on its metal part.

The results obtained are given in table I below.

$V_{in}$ (mV) is the input voltage at the Prana type power amplifier 130. $P_d$ and $P_r$ are, respectively, the direct and reflected powers read on wattmeter 132. $P_{Trans}$ being the power transmitted by the transducer ($P_{Trans}=P_d-P_r$). Lum is the luminescence value read on nanoammeter 186. The indices C and NC respectively characterize a random or pseudo-random (A.S.) type coded signal according to the invention (FIGS. 3 and 4) and an uncoded signal, in other words an S1-type sinewave according to the prior art (FIGS. 1 and 2).

The luminescence values obtained from a signal coded according to the invention are shown by line 2 with diamond-shaped points in FIG. 6, line 1 joining the circles or dots giving the figures for a sinewave uncoded signal according to the prior art in FIG. 6, as a function of signal power transmitted by the transducer, in Watts. For values below 10 W, the luminescence measured for the two signals corresponds to the natural luminescence of water.

The cavitation threshold was obtained around 12 to 15 W for the uncoded signal of the continuous sinewave type of the prior art whereas this was never reached in the range of power employed with random or pseudo-random type coded signal according to the present invention.

It was not possible to make measurements above 40 W without putting the ultrasound transducer 123 at risk.

| Vin (mV) | PdNc (W) | PrNc (W) | PdC (W) | PrC (W) | LumNC (nA) | LumC (nA) | $P_{Trans}^{NC}$ (W) | $P_{Trans}^{C}$ (W) |
|---|---|---|---|---|---|---|---|---|
| 34 | 13,0 | 0,6 | 31,5 | 19,0 | 29 | 49 | 12,4 | 12,5 |
| 39 | 15,3 | 0,6 | 39,5 | 24,1 | 130 | 61 | 14,7 | 15,4 |
| 44 | 20,0 | 0,9 | 50,8 | 31,1 | 600 | 71 | 19,1 | 9,7 |
| 49 | 26,3 | 1,5 | 61,2 | 37,2 | 1400 | 78 | 24,8 | 24,0 |
| 55 | 32,1 | 1,7 | 77,8 | 47,8 | 2600 | 95 | 30,4 | 30,0 |
| 62 | 41,0 | 2,2 | 98,3 | 59,6 | 4325 | 89 | 38,8 | 38,7 |

Thus, it can be seen that, unexpectedly, by using a wideband electronic signal according to the present invention and, for example, a pseudo-random or random type coded electronic signal, no cavitation phenomena appear in the range of powers used for the experiment, this being reflected by the set of steady values for luminescence as a function of power, in contrast to line 1 obtained with a sinewave signal of the prior art.

This constitutes a surprising result of the present invention.

Figure 7:
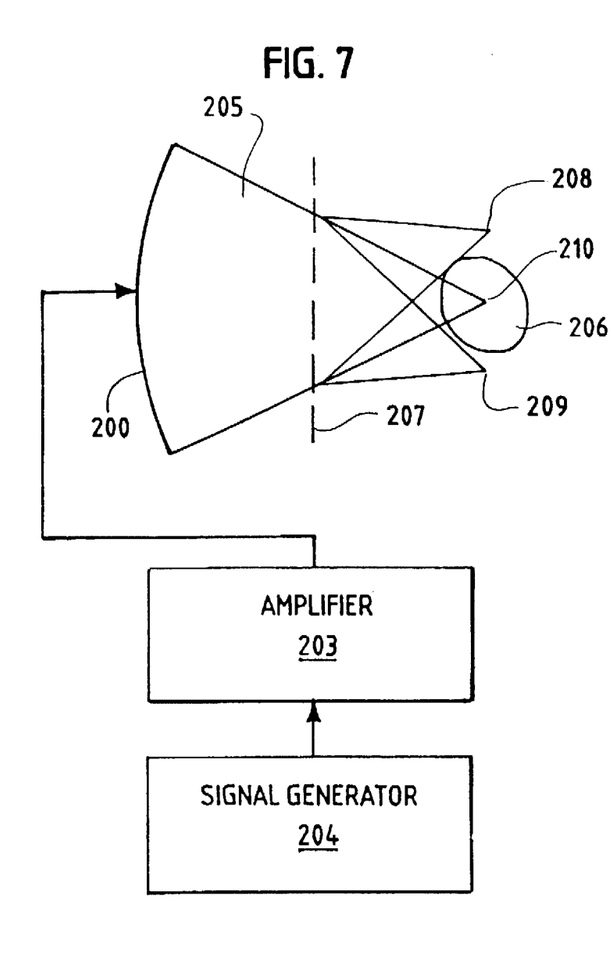
FIG. 7 shows schematically the operation of a prior art device in the presence of a periodic or quasi-periodic structure.

FIG. 7 is a highly schematic representation of the operation of a device according to the prior art, in the presence of a periodic or quasi-periodic structure; in FIG. 7, a therapy device 200 linked via an amplifier 203 to a signal generator 204 can be seen.

As mentioned above, the therapy device is for example a semi-spherical cup with natural focusing, comprising one or several transducer elements (a single transducer, or a set of annular or mosaic ceramic elements).

The therapy device sets up an ultrasound field 205 directed towards the treatment region 206. A periodic or quasi-periodic structure 207 is disposed in the ultrasound field 205 between a therapy device 200 and the treatment region 206, reference 210 identifying the focal spot. This structure can for example be the rib cage, in the case of external treatment of tumors of the liver.

In devices of the prior art driven by a conventional sinewave type signal or, more generally, excited by periodic signals, such a periodic structure leads to the appearance of secondary points of focus 208, 209 (or side lobes) outside the treatment region as a result of diffraction of the ultrasound waves passing through structure 207. The appearance of such secondary points of focus has obvious consequences for the safety of treatment. Moreover, radiation of energy to these secondary points decreases the power radiated to focal point 210, and can compromise the effectiveness of treatment. One can say that in this configuration, secondary focusing phenomena occur behind the periodic or quasi-periodic structure. In this specification, the expression "behind the periodic or quasi-periodic structure 207" should be taken to mean "downstream, regarding the propagation path of ultrasound waves, of the periodic or quasi-periodic structure 207".

Figure 8:
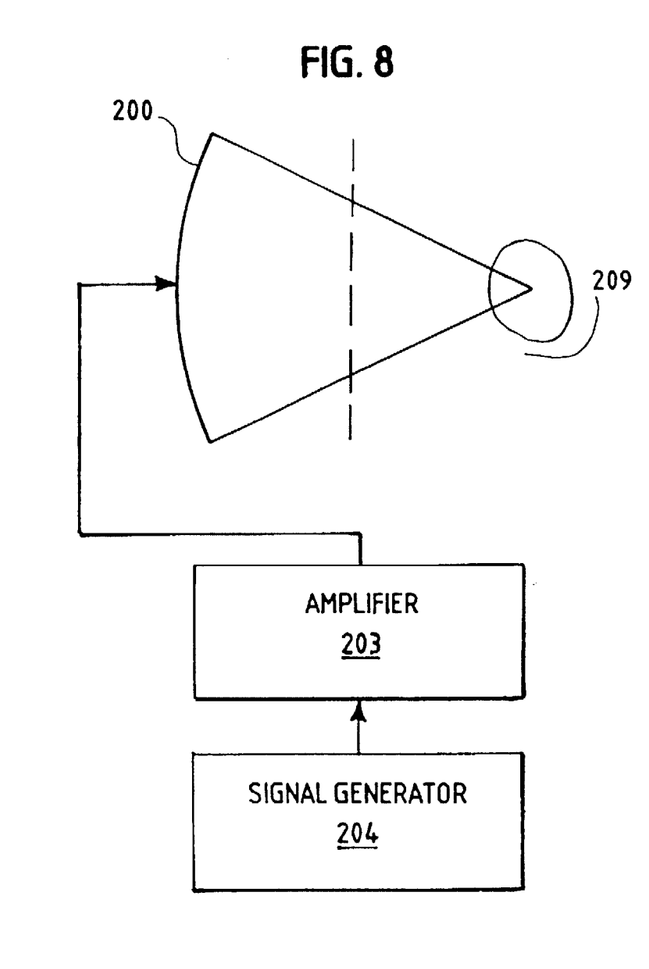
FIG. 8 is a schematic representation similar to that in FIG. 7 in a device implementing the invention.

FIG. 8 shows the same arrangement as in FIG. 7 in a device implementing the invention. The invention discloses the use of a signal generator supplying a wideband electronic signal for exciting the therapy device. As described above, the signal generator may supply a random or pseudo-random electronic signal and, more particularly, a Golay or Barker coded pseudo-random electronic signal or an M-sequence pseudo-random coded type electronic signal (of the type described above for example).

The invention can also be characterized in that the therapy device is excited by a signal having an auto-correlation function that is as close as possible to a Dirac function. The signals above have an auto-correlation function which approaches that of a Dirac function.

FIG. 8 illustrates the results of the invention: the secondary points of focus caused by the periodic or quasi-periodic structure have disappeared; the position of such focal points does in fact essentially depend on the periodicity of the structure 207 and the ultrasound frequency. The use of wideband signals causes the position of the secondary point of focus to vary during the course of treatment. In this way, there is no longer a local build-up of energy outside the treatment region in the area surrounding the principal point of focus 210. The invention thus makes it possible to decrease the risk of producing secondary lesions outside the treatment region, even in the presence of a periodic or quasi-periodic structure.

The invention makes it possible to achieve accurate and localised treatment, even behind a periodic or quasi-periodic structure such as, for example, treatment of the liver behind the rib cage.

The various embodiments of the invention described with reference to the preceding figures can obviously be combined.

The present invention obviously includes all means constituting technical equivalents of the means described, as well as various combinations thereof.

Moreover, FIGS. 3 to 6 constitute an integral part of this invention and thus of the description.

What is claimed is:

1. A method for generating high power therapeutic ultrasound waves in a propagation medium, said ultrasound waves produced by an ultrasonic transducer having at least one ultrasound transducer element, the method comprising the steps of activating said at least one ultrasound transducer element with an electronic signal supplied by a signal generator, the signal generator supplying a wideband electronic signal to said at least one ultrasound transducer element, said wideband signal having a multiple frequency spectrum, the wideband signal configured to reduce or prevent cavitation phenomena resulting from the propagation of the ultrasound waves emitted by said at least one ultrasound transducer element within the propagation medium.

2. The method according to claim 1, wherein said signal generator is a signal generator supplying a random or pseudo-random electronic signal.

3. The method according to claim 1, wherein said signal generator is a signal generator supplies a Golay coded pseudo-random electronic signal.

4. The method according to claim 1, wherein said signal generator supplies a Barker coded pseudo-random electronic signal.

5. The method according to claim 1, wherein said signal generator supplies a M-sequence pseudo-random type coded electronic signal.

6. The method according to claim 5, wherein said M-sequence pseudo-random type coded electronic signal has an elementary pulse duration of about 1 μs and a period of repetition T of about between 0.5 and 5 s.

7. The method according to claim 5, wherein said M-sequence pseudo-random type coded electronic signal has an elementary pulse duration of about between 0.1 μs and 100 μs and a period of repetition T of about between 1 μs and 10 s.

8. A therapy apparatus for generating high power ultrasound waves comprising an ultrasonic transducer having at least one ultrasound therapy transducer element and a signal generator supplying an electronic signal to said at least one ultrasound therapy transducer element, wherein said signal generator supplies a wideband electronic signal, said wideband signal having a multiple frequency spectrum and being of a random or pseudo-random type.

9. The therapy apparatus according to claim 8, wherein said signal generator supplies a Gaussian or Poissonian distribution type random signal.

10. The therapy apparatus according to claim 8, wherein said signal generator supplies an M-sequence pseudo-random type coded electronic signal.

11. The therapy apparatus according to claim 10, wherein said M-sequence pseudo-random type coded electronic signal has an elementary pulse duration of about 1 μs and a period of repetition T of about between 0.5 s and 5 s.

12. The therapy apparatus according to claim 10, wherein said M-sequence pseudo-random type coded electronic signal has an elementary pulse duration of about between 0.1 μs and 100 μs and a period of repetition T of about between 1 μs and 10 s.

13. The therapy apparatus according to claim 8, wherein said signal generator supplies a Golay coded or Barker coded pseudo-random signal.

14. The therapy apparatus according to claim 8, wherein said at least one ultrasound transducer element is a wideband transducer element.

15. The therapy apparatus according to claim 8, wherein said ultrasound transducer is selected from the group consisting of a single element, an annular array and a mosaic of ultrasound therapy transducer elements, said ultrasound transducer being of the focused type, configured to use geometrical focusing, and being in the form of a semi-spherical cup.

16. The therapy apparatus according to claim 8, wherein said ultrasound transducer is a wideband transducer selected from the group consisting of a single element, an annular array and a mosaic of ultrasound therapy transducer elements, said ultrasound transducer being of the focused type, configured to use geometrical focusing, and being in the form of a semi-spherical cup.

17. A method for treatment using high power ultrasound therapy waves, the method comprising the steps of supplying a wideband electronic signal to an apparatus, the apparatus comprising an ultrasonic transducer having at least one ultrasound transducer element and a signal generator for supplying the wideband electronic signal to said at least one ultrasound transducer element, said wideband signal having a multiple frequency spectrum and configured to reduce or prevent secondary focusing phenomena behind a periodic or quasi-periodic structure.

18. The method according to claim 17, wherein said wideband electronic signal is of the random or pseudo-random type.

19. The method according to claim 17, wherein said wideband electronic signal is a Gaussian or Poissonian distribution type random signal.

20. The method according to claim 17, wherein said wideband electronic signal is a Barker coded or Golay coded pseudo-random signal.

21. The method according to claim 17, wherein said wideband electronic signal is a M-sequence pseudo-random type coded electronic signal of a frequency having an elementary pulse duration of about between 0.1 μs and 100 μs and a period of repetition T of about between 1 μs and 10 s.

22. The method according to claim 17, wherein said wideband electronic is a M-sequence pseudo-random type coded electronic signal if a frequency having an elementary pulse duration of about 1 μs and a period of repetition T of about between 0.5 s and 5 s.

* * * * *